United States Patent

Kirsch et al.

[11] Patent Number: 5,911,912
[45] Date of Patent: Jun. 15, 1999

[54] HALOVINYL ETHERS

[75] Inventors: Peer Kirsch, Darmstadt; Joachim Krause, Dieburg; Kazuaki Tarumi, Seeheim, all of Germany

[73] Assignee: Merck Patent Gesellschaft mit beschraenkter Haftung, Germany

[21] Appl. No.: 08/975,198

[22] Filed: Nov. 20, 1997

[30] Foreign Application Priority Data

Nov. 20, 1996 [DE] Germany ............ 196 47 991

[51] Int. Cl.$^6$ .......... C09K 19/30; C09K 19/34; C07D 319/06; C07C 41/01
[52] U.S. Cl. .......... 252/299.01; 252/299.61; 252/299.63; 549/369; 549/370; 549/374; 568/655; 568/661; 568/669
[58] Field of Search .......... 252/299.01, 299.61, 252/299.62, 299.63, 299.64, 299.66, 299.67; 549/369, 370, 374; 568/655, 661, 669

[56] References Cited

U.S. PATENT DOCUMENTS

| | | | |
|---|---|---|---|
| 4,877,548 | 10/1989 | Kitano et al. | 252/299.63 |
| 5,403,512 | 4/1995 | Bartmann et al. | 252/299.01 |
| 5,723,682 | 3/1998 | Poetsch et al. | 568/655 |
| 5,800,735 | 9/1998 | Poetsch et al. | 252/299.61 |

OTHER PUBLICATIONS

CAPLUS 1997: 127433.
Derwent Abstract of DE 4 238 377, 1994.

*Primary Examiner*—Shean C. Wu
*Attorney, Agent, or Firm*—Millen, White, Zelano, & Branigan, P.C.

[57] ABSTRACT

Halovinyl ethers of the general formula I

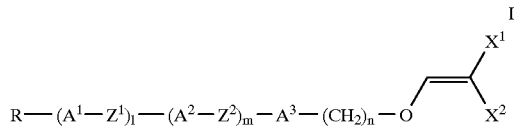

in which R, $A^1$, $A^2$, $A^3$, $Z^1$, $Z^2$, $X^1$, $X^2$, l, m and n are as defined herein are suitable as components of liquid-crystalline media.

13 Claims, No Drawings

HALOVINYL ETHERS

The invention relates to halovinyl ethers of general formula I

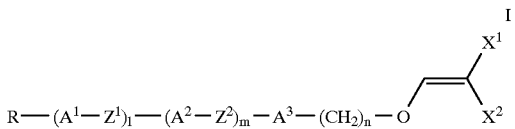

in which
R is alkyl or alkenyl having 1 to 12 carbon atoms, in each of which one or more $CH_2$ groups may be replaced by —O—, —$CF_2$— or —CH=CH—, or one or two CH groups may be replaced by CF, in such a way that two oxygen atoms are not linked to one another, $A^1$, $A^2$ and $A^3$ are each, independently of one another,
  a) a trans-1,4-cyclohexylene radical, in which, in addition, one or more non-adjacent $CH_2$ groups may be replaced by —O— and/or —S—,
  b) a 1,4-phenylene radical, in which, in addition, one or two CH groups may be replaced by N,
  c) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, or
  d) 1,4-cyclohexenylene,
where the radicals a), b) and d) may be substituted by one or two Cl or F atoms, $Z^1$ and $Z^2$ are each, independently of one another —CO—O—, —O—CO—, —$CH_2$O—, —O—$CH_2$—, —$CH_2CH_2$—, —CH=CH—, —C≡C— or a single bond, $X^1$ and $X^2$ are each, independently of one another, H, Cl or F, l and m are each, independently of one another, 0, 1 or 2, where l+m is ≧1, and n is 1, 2 or 3.

The invention furthermore relates to the use of these compounds as components of liquid-crystalline media and to liquid-crystal and electro-optical display elements which contain the novel liquid-crystalline media.

The compounds of the formula I can be used as components of liquid-crystalline media, in particular for displays based on the principle of the twisted cell, the guest-host effect, the effect of deformation of aligned phases or the effect of dynamic scattering.

The novel compounds are preferably employed in matrix liquid-crystal displays (MLCDs). Examples of nonlinear elements which can be used to individually switch the individual pixels are active elements (i.e. transistors). This is then referred to as an "active matrix", and a differentiation can be made between two types:
  1. MOS (metal oxide semiconductor) transistors on a silicone wafer as substrate.
  2. Thin-film transistors (TFTs) on a glass plate as substrate.

The use of microcrystalline silicon as substrate material limits the display size since even modular assembly of the various part displays results in problems at the joints.

In the case of the more promising type 2, which is preferred, the electro-optical effect used is usually the TN effect. A differentiation is made between two technologies: TFTs comprising compound semiconductors, such as, for example, CdSe, or TFTs based on polycrystalline or amorphous silicon.

The TFT displays usually operate as TN cells with crossed polarizers in transmission mode and are illuminated from the back.

The term MLC displays here covers any matrix display with integrated nonlinear elements, i.e. in addition to the active matrix, also displays containing passive elements, such as varistors or diodes (MIM=Metal-Insulator-Metal).

DE 42 38 377 discloses difluorovinyl ethers for use in liquid-crystal displays. However, the difluorovinyl ether group in the compounds described therein is linked directly to an aromatic ring.

EP 0 325 796 describes liquid-crystalline compounds in which a cyclohexane ring is linked to a difluorovinyl group. However, these compounds have been found to be unstable and tend to decompose with elimination of HF.

The invention therefore had an object of finding novel, stable, liquid-crystalline or mesogenic compounds which are suitable as components of liquid-crystalline media and in particular simultaneously have comparatively low viscosity and are stable to heat and to UV irradiation.

Upon further study of the specification and appended claims, further objects and advantages of this invention will become apparent to those skilled in the art.

It has been found that compounds of the formula I are eminently suitable as components of liquid-crystalline media. In particular, they have high nematogeniety and comparatively low viscosities. They can be used to obtain stable liquid-crystalline media having a broad mesophase range and advantageous optical and dielectric anisotropy values. These media furthermore have very good low-temperature behavior.

In addition, the provision of compounds of the formula I very generally considerably broadens the range of liquid-crystalline substances which are suitable for various applicational points of view for the preparation of liquid-crystalline mixtures.

The compounds of the formula I have a broad range of applications. Depending on the choice of substituents, these compounds can be used as base materials of which liquid-crystalline media are predominantly composed. However, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature. range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystalline display elements, in particular electro-optical display elements, and in particular AMD displays, which contain such media.

Above and below, R, $A^1$, $A^2$, $A^3$, $Z^1$, $Z^2$, $X^1$, $X^2$, l, m and n have the definition given, unless expressly stated otherwise.

For simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bco denotes a bicyclo[2.2.2]octylene radical, where Cyc and/or Phe may be unsubstituted or monosubstituted or polysubstituted by Cl, F or CN.

W below denotes the following group:

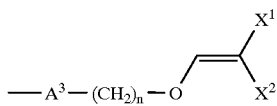

The compounds of formula I include bicyclic compounds of the subformulae Ia and Ib:

| | |
|---|---|
| R—A²—W | Ia |
| R—A²—Z²—W | Ib | tricyclic compounds of the subformulae Ic to If:

| | |
|---|---|
| R—A¹—A²—W | Ic |
| R—A¹—A²—Z²—W | Id |
| R—A¹—Z¹—A²—W | Ie |
| R—A¹—Z¹—A²—Z²—W | If | and tetracyclic compounds of the subformulae Ig to In:

| | |
|---|---|
| R—A¹—A¹—A²—W | Ig |
| R—A¹—Z¹—A¹—A²—W | Ih |
| R—A¹—A¹—Z¹—A²—W | Ii |
| R—A¹—A¹—A²—Z²—W | Ij |
| R—A¹—Z¹—A¹—Z¹—A²—W | Ik |
| R—A¹—Z¹—A¹—A²—Z²—W | Il |
| R—A¹—A¹—Z¹—A²—Z²—W | Im |
| R—A¹—Z¹—A¹—Z¹—A²—Z²—W | In |

Of these, particular preference is given to those of the subformulae Ia, Ic, Id, Ie, Ig, Ih and Ii.

The preferred compounds of the subformula Ia include those of the subformulae Iaa and Iab:

| | |
|---|---|
| R—Phe—W | Iaa |
| R—Cyc—W | Iab |

The preferred compounds of the subformula Ib include those of the subformulae Iba to Ibc:

| | |
|---|---|
| R—Phe—Z²—W | Iba |
| R—Cyc—Z²—W | Ibb |
| R—Dio—Z²—W | Ibc |

The preferred compounds of the subformula Ic include those of the subformulae Ica to Icg:

| | |
|---|---|
| R—Cyc—Cyc—W | Ica |
| R—Cyc—Phe—W | Icb |
| R—Phe—Dio—W | Icc |
| R—Phe—Phe—W | Icd |
| R—Phe—Cyc—W | Ice |
| R—Dio—Dio—W | Icf |
| R—Pyr—Phe—W | Icg |

Of these, those of the formulae Ica, Icb, Icc and Icf are particularly preferred.

The preferred compounds of the subformula Id include those of the subformulae Ida to Idg:

| | |
|---|---|
| R—Cyc—Cyc—Z²—W | Ida |
| R—Cyc—Phe—Z²—W | Idb |
| R—Phe—Phe—Z²—W | Idc |
| R—Dio—Phe—Z²—W | Idd |
| R—Dio—Dio—Z²—W | Ide |
| R—Cyc—Phe—CH₂CH₂—W | Idf |
| R—A¹—Phe—CH₂CH₂—W | Idg |

The preferred compounds of the subformula Ie include those of the subformulae Iea to IeH:

| | |
|---|---|
| R—Cyc—Z¹—Cyc—W | Iea |
| R—A¹—CH₂CH₂—A²—W | Ieb |
| R—Cyc—Z¹—Ph—W | Iec |
| R—A¹—OCO—Phe—W | Ied |
| R—Phe—Z¹—Phe—W | Iee |
| R—Pyr—Z¹—A²—W | Ief |
| R—Pyd—Z¹—A²—W | Ieg |
| R—Dio—Z¹—A²—W | Ieh |

Of these, those of the subformulae Iea, Ieb, Iec and Iee are particularly preferred.

Preferred compounds of the subformula If include those of the subformulae Ifa to Ife:

| | |
|---|---|
| R—Phe—CH₂CH₂—Z²—W | Ifa |
| R—A¹—COO—Phe—Z²—W | Ifb |
| R—Cyc—Z¹—Cyc—Z²—W | Ifc |
| R—Phe—Z¹—Phe—Z²—W | Ifd |
| R—Cyc—CH₂CH₂—Phe—Z²—W | Ife |

The preferred compounds of the subformulae Ig to In include those of the subformulae Io to Iv:

| | |
|---|---|
| R—A¹—Cyc—Cyc—W | Io |
| R—A¹—Cyc—Phe—W | Ip |
| R—A¹—CH₂CH₂—A¹—Phe—W | Iq |
| R—Cyc—Z¹—A¹—Z¹—Phe—W | Ir |
| R—Phe—Phe—Phe—W | Is |
| R—Phe—Z¹—A¹—Phe—W | It |
| R—A¹—Phe—Z¹—Phe—W | Iu |
| R—A¹—Z¹—Cyc—Phe—Z²—W | Iv |

In the compounds of the formulae above and below, R is preferably alkyl or alkenyl, furthermore, preferably alkoxy.

Preference is given to compounds of the formula I in which R is an alkyl radical, in which one or more $CH_2$ groups may be replaced by —O— or $CF_2$.

$A^1$, $A^2$ and $A^3$, independently of one another, are preferably Phe, Cyc, Che, Pyd, Pyr or Dio. The compounds of the formula I preferably contain not more than one of the radicals Bco, Pyd, Pyr, Dio and Dit.

In the compounds of the formula I, preference is given to the stereoisomers in which the rings Cyc and piperidine are trans-1,4-disubstituted. The formulae which contain one or more groups Pyd, Pyr and/or Dio in each case include the two 2,5-positional isomers or the two trans-2,5-positional isomers.

If more than one ring $A^1$ is present, the rings may have identical or different meanings. The same also applies to all other groups which occur more than once.

Preference is also given to compounds of the formula I and all subformulae in which $A^1$ and/or $A^2$ and/or $A^3$ is 1,4-phenylene which is monosubstituted or disubstituted by F or CN.

$A^1$, $A^2$ and $A^3$ are preferably

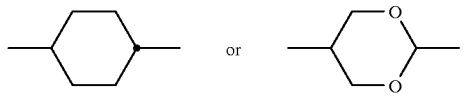

l and m are preferably 0 or 1, n is preferably 1, $Z^1$ and $Z^2$, independently of one another, are preferably —CH$_2$CH$_2$—, —CO—O—, —O—CO— or a single bond, particularly preferably a single bond. Preference is given to compounds of the formula I in which $Z^1$ and/or $Z^2$ is a single bond.

Particular preference is given to compounds of the formula I in which n is 1 and $A^3$ is

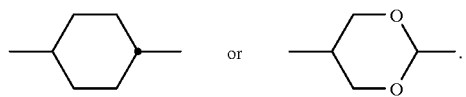

The 1,4-cyclohexenylene group preferably has one of the following structures:

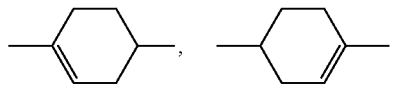

$X^1$ and $X^2$ are preferably F or Cl, particularly preferably F.

The compounds of the formula I include the preferred compounds of the subformulae Ia to Iq:

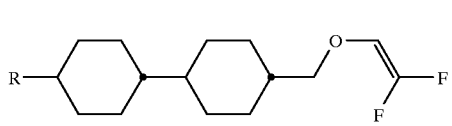

Ia

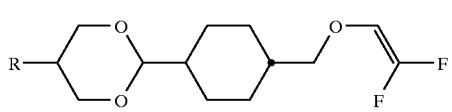

Ib

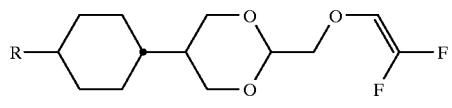

Ic

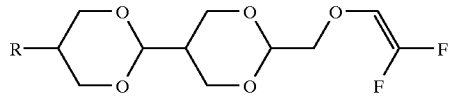

Id

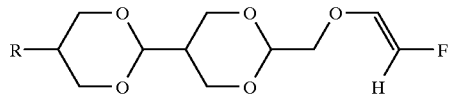

Ie

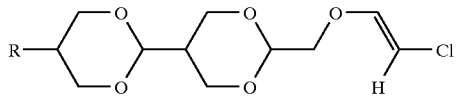

If

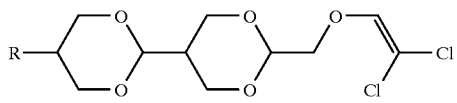

Ig

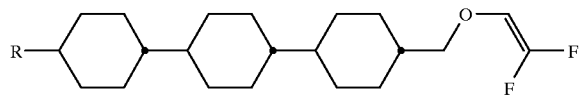

Ih

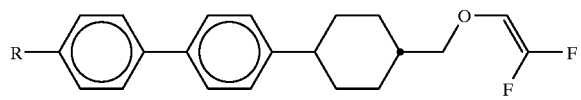

Ii

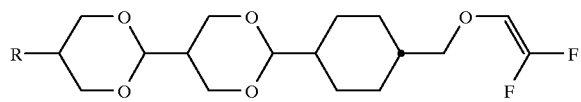

Ij

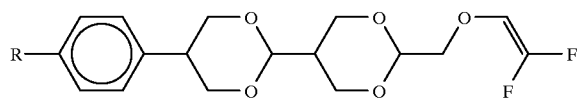

Ik

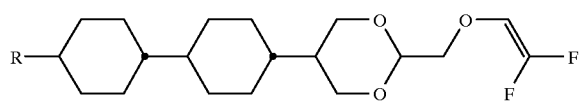

Il

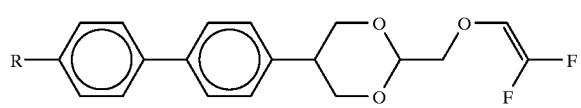

Im

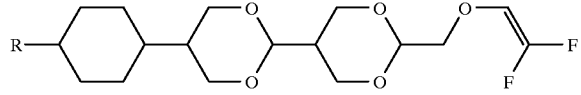

In

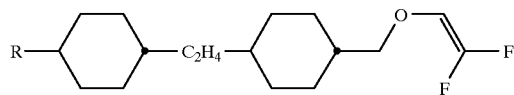

Io

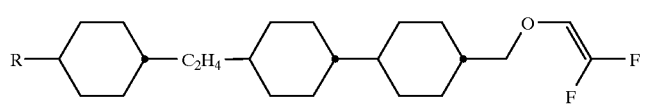

Ip

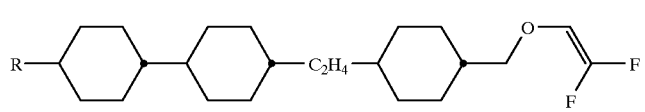

Iq in which R is as defined above. Particular preference is given to subformulae Ia, Ib, Ic and Id.

If R is an alkyl radical and/or an alkoxy radical, it may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, methoxy, octoxy, nonoxy, decoxy, undecoxy or dodecoxy.

Oxaalkyl is preferably straight-chain 2-oxapropyl (=methoxymethyl), 2-oxabutyl (=ethoxymethyl) or 3-oxybutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If R is an alkenyl radical, this may be straight-chain or branched. It is preferably straight-chain and has 2 to 10 carbon atoms. Accordingly, it is in particular vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl. Particular preference is given to the vinyl group and trans-alk-1-enyl radicals.

If R is an alkyl or alkenyl radical in which one or more $CH_2$ groups have been replaced by $CF_2$, this radical is preferably straight-chain. In the case of multiple substitution, the resultant radicals also include perfluorinated radicals. In the case of monosubstitution, the fluorine substituent can be in any desired position, but is preferably in the ω-position.

Compounds of the formula I containing branched wing groups R may occasionally be of importance owing to better solubility in the conventional liquid-crystal-line base materials, but in particular as chiral dopants if they are optically active. Smectic compounds of this type are suitable as components of ferroelectric materials.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers both the racemates of these compounds and the optical antipodes, and mixtures thereof.

Of these compounds of the formula I and the subformulae, preference is given to those in which at least one of the radicals present therein has one of the preferred meanings indicated.

In the compounds of the formula I, preference is given to the stereoisomers in which the cyclohexane ring is trans-1, 4-disubstituted. The compounds of the formula I are prepared by methods known per se, and described in the literature (for example in the standard works, such as Houben-Weyl, Methoden der Organischen Chemie, Georg-Thieme-Verlag, Stuttgart), to be precise under reaction conditions which are known and are suitable for said reactions.

Use can also be made here of variants which are known per se, but are not described here in further detail.

If desired, the starting materials can also be formed in situ by not isolating them from the reaction mixture, but instead immediately converting them into the compounds of the formula I.

The novel oligo-1,3-dioxane derivatives are readily accessible by forming the 1,3-dioxane ring by acid-catalyzed reaction of a corresponding diol or bis(trialkylsilyl) ether with an aldehyde.

The diols of the formula

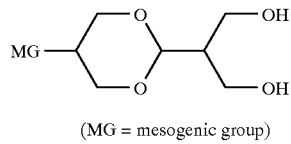

(MG = mesogenic group)

employed as starting compounds are either known or can be prepared by known methods (see, for example, DE 195 25 314.0).

The acetal synthesis starting from bisilyl ethers and carbonyl compounds is known per se.

Suitable variants of this reaction are given in the literature (see, for example, R. Noyori, S. Murata, M. Suzuki, Tetrahedron 1981, 37, 3899–3910; F. A. Carey, R. J. Sundberg, Advanced Organic Chemistry, $3^{rd}$ Edn., Part B: Reactions and Synthesis, Plenum Press, New York, 1993, p. 689 and the references cited therein).

The novel compounds can be prepared, for example, in accordance with the following reaction schemes:

Scheme 1

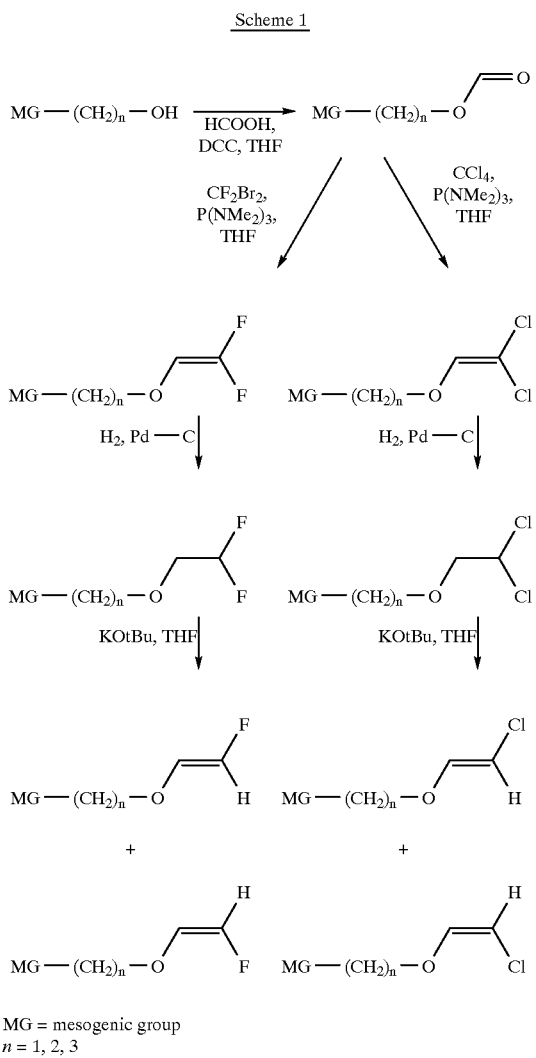

MG = mesogenic group
$n = 1, 2, 3$

Scheme 2

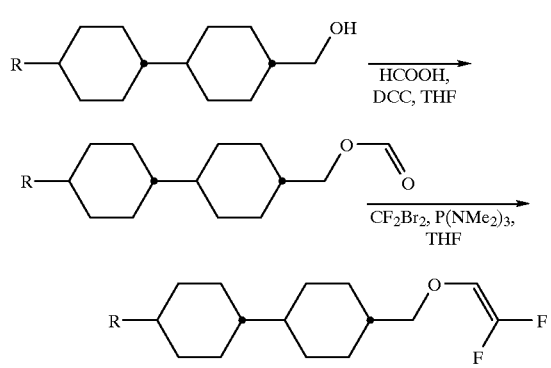

Scheme 3

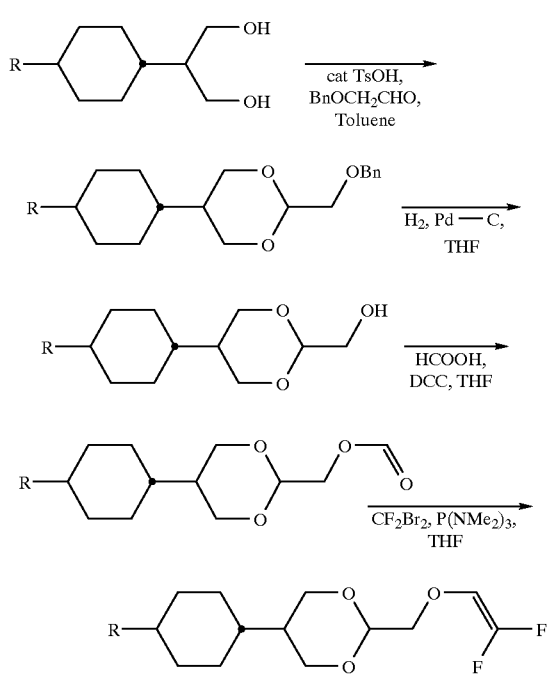

Scheme 4

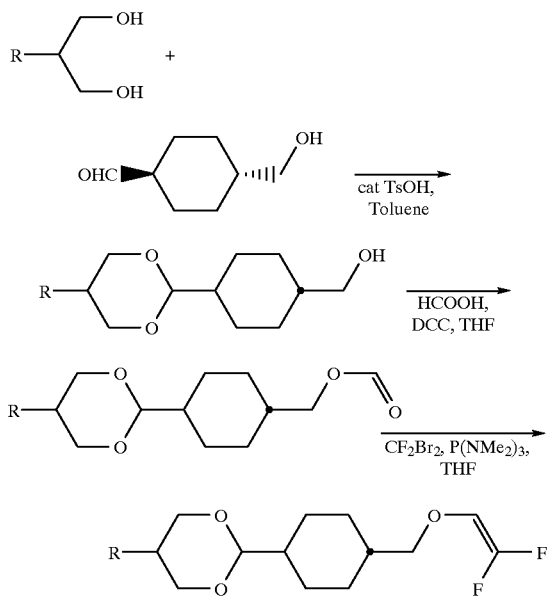

Scheme 5

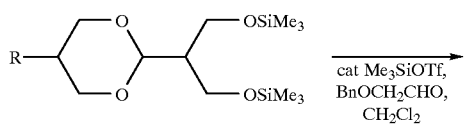

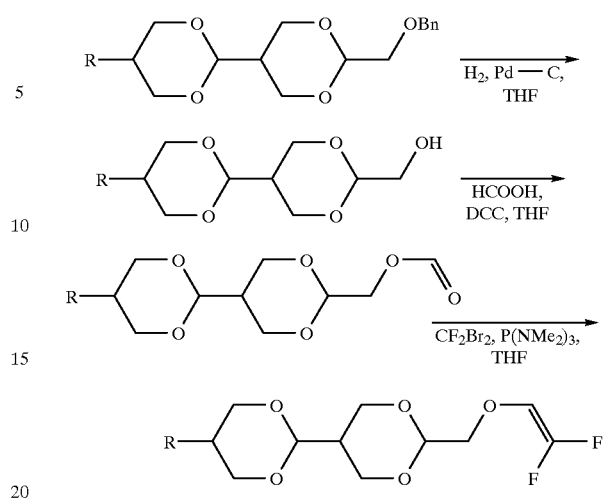

Esters of the formula I can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols and phenols are known or can be prepared analogously to known processes.

Particularly suitable reactive derivatives of said carboxylic acids are the acid halides, in particular the chlorides and bromides, furthermore the anhydrides, azides or esters, in particular alkyl esters having 1–4 carbon atoms in the alkyl group.

Particularly suitable reactive derivatives of said alcohols or phenols are the corresponding metal alkoxides or phenoxides, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulphoxides, such as dimethyl sulphoxide or sulpholane. Water-miscible solvents can at the same time advantageously be used for removal by azeotropic distillation of the water formed during the esterification. It may in some cases also be possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are generally complete after from 15 minutes to 48 hours.

In detail, the reaction conditions for the esterification depend substantially on the nature of the starting materials used. Thus, the reaction of a free carboxylic acid with a free alcohol or phenol is generally carried out in the presence of a strong acid, for example a mineral acid, such as hydrochloric acid or sulphuric acid. A preferred reaction procedure is to react an acid anhydride or, in particular, an acyl chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogen carbonate, potassium carbonate or potassium hydrogen carbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification comprises first converting the alcohol or the phenol into the sodium or potassium alkoxide or phenoxide, for example by treatment with ethanolic sodium hydroxide or potassium hydroxide solution, and isolating and reacting the product with an acid anhydride or, in particular, acyl chloride.

Nitriles can be obtained by replacement of halogens by copper cyanide or alkali metal cyanide.

In a further process for the preparation of compounds of the formula I in which $Z^1$ or $Z^2$ is —CH=CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, are also suitable as solvent. Examples of suitable palladium catalysts are palladium salts, in particular Pd(II) acetate, with organophosphorus(III) compounds, such as, for example, triarylphosphines. The reaction can be carried out in the presence or absence of an inert solvent at temperatures between about 0° C. and 150° C., preferably between 20° C. and 100° C.; examples of suitable solvents are nitriles, such as acetonitrile, or hydrocarbons, such as benzene or toluene. The aryl halides and olefins employed as starting materials are frequently commercially available or can be prepared by methods known from the literature, for example by halogenation of corresponding parent compounds or by elimination reactions on corresponding alcohols or halides.

This method allows the preparation of, for example, stilbene derivatives. The stilbenes may also be prepared by reacting a 4-substituted benzaldehyde with a corresponding phosphorus ylide by the Wittig method. However, tolans of the formula I can also be prepared by employing monosubstituted acetylene instead of the olefin (Synthesis 627 (1980) or Tetrahedron Lett. 27, 1171 (1986)).

Furthermore, aromatic compounds may furthermore be coupled by reacting aryl halides with aryl tin compounds. These reactions are preferably carried out with addition of a catalyst, such as, for example, a palladium (0) complex, in inert solvents, such as hydrocarbons, at high temperatures, for example in boiling xylene, under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which $Z^1$ or $Z^2$ is —C≡C— can also be prepared by the Fritsch-Buttenberg-Wiechell rearrangement (Ann. 279, 319, 1984), in which 1,1-diaryl-2-haloethylenes are rearranged in the presence of strong bases to give diarylacetylenes.

Tolans of the formula I, can also be prepared by brominating the corresponding stilbenes and subsequently subjecting the brominated stilbenes to a dehydrohalogenation reaction. Use can also be made here of variants of this reaction which are known per se, but are not mentioned here in greater detail.

Ethers of the formula I can be obtained by etherification of corresponding hydroxyl compounds, preferably of corresponding phenols, the hydroxyl compound advantageously first being converted into a corresponding metal derivative, for example into the corresponding alkali metal alkoxide or alkali metal phenoxide, by treatment with NaH, NaNH$_2$, NaOH, KOH, Na$_2$CO$_3$ or K$_2$CO$_3$. This metal derivative can then be reacted with the appropriate alkyl halide, alkyl sulphonate or dialkyl sulphate, advantageously in an inert solvent, such as, for example, acetone, 1,2-dimethoxyethane, DMF or dimethyl sulphoxide or alternatively with an excess of aqueous or aqueous-alcoholic NaOH or KOH, at temperatures between about 20° C. and 100° C.

In order to prepare the laterally substituted fluorine or chlorine compounds of the formula I, corresponding analine derivatives can be reacted with sodium nitrite and either with tetrafluoroboric acid (in order to introduce an F atom) or with copper (I) chloride (in order to introduce a Cl atom) to give the diazonium salts, which are then thermally decomposed at temperatures of 100–140° C.

The linking of an aromatic ring to a nonaromatic ring or of two nonaromatic rings is preferably obtained by condensation of an organolithium or organomagnesium compound with a ketone.

The organometallic compounds are prepared, for example, by metal-halogen exchange (for example in accordance with Org. React. 6, 339–366 (1951)) between the corresponding halogen compound and an organolithium compound, such as, preferably, tert-butyl lithium or lithium naphthaleneide, or by reaction with magnesium turnings.

The linking of two aromatic rings or of an aliphatic group $Z^1$ or $Z^2$ with an aromatic ring is preferably carried out by Friedel-Crafts alkylation or acylation by reacting the corresponding aromatic compounds with catalysis by a Lewis acid. Suitable Lewis acids are, for example, SnCl$_4$, ZnCl$_2$ or, in particular, AlCl$_3$ and TiCl$_4$.

The linking of two aromatic rings can furthermore be carried out by the Ullmann reaction (for example Synthesis 1974, p. 9) between aryl iodides and copper iodides, but preferably between an aryl copper compound and an aryl iodide, or by the Gomberg-Bachmann reaction between an aryl diazonium salt and the corresponding aromatic compound (for example Org. React. 2, 224 (1944)). The tolans of the formula I($Z^1$ or $Z^2$=—C≡C—) are prepared, for example, by reacting the corresponding aryl halides with an acetylide in a basic solvent with transition-metal catalysis; palladium catalysts can preferably be used here, in particular a mixture of bis(triphenylphosphine)palladium(II) chloride and copper iodide in piperidine as solvent.

Furthermore, the compounds of the formula I can be prepared by reducing a compound which contains one or more reducible groups and/or C—C bonds in place of H atoms, but otherwise conforms to the formula I.

Suitable reducible groups are preferably carbonyl groups, in particular keto groups, furthermore, for example, free or esterified hydroxyl groups or aromatically bonded halogen atoms. Preferred starting materials for the reduction are compounds which conform to the formula I, but contain a cyclohexene ring or cyclohexanone ring in place of a cyclohexane ring and/or contain a —CH=CH— group in place of a —CH$_2$CH$_2$— group and/or contain a —CO— group in place of a —CH$_2$— group and/or contain a free or functionally derived (for example in the form of its p-toluenesulfonate) OH group in place of an H atom.

The reduction can be carried out, for example, by catalytic hydrogenation at temperatures between about 0° C. and about 200° C. and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are expediently noble metals, such as Pt or Pd, which may be employed in the form of oxides (for example PtO$_2$ or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, expediently in aqueous-alcoholic solution or in the heterogeneous phase with water/toluene at temperatures between about 80 and 120°) or Wolff-Kishner (using hydrazine, expediently in the presence of alkali, such as KOH or NaOH, in a high-boiling solvent, such as diethylene glycol or triethylene glycol, at temperatures between about 100 and 200°) to give the corresponding compounds of the formula I which contain alkyl groups and/or —CH$_2$CH$_2$— bridges.

Furthermore, reductions using complex hydrides are possible. For example, arylsulfonyloxy groups can be removed reductively using LiAlH$_4$, in particular p-toluenesulfonyloxymethyl groups can be reduced to methyl groups, expediently in an inert solvent at temperatures between about 0 and 100°. Double bonds can be hydrogenated using tributyltin hydride in methanol.

The starting materials are either known or can be prepared analogously to known compounds.

The term mesogenic group is known to the person skilled in the art (for example H. Kelker/R. Hatz, Handbook of Liquid Crystals, Verlag Chemie, Weinheim, 1980) and denotes a "rod-like" radical consisting of ring members, optionally bridging members and wing groups. The novel liquid-crystalline media preferably comprise 2 to 40, in particular 4 to 30, components as further constituents besides one or more novel compounds. These media very particularly preferably comprise 7 to 25 components besides one or more novel compounds. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, trans-1,2-dicyclohexylethenes, 1-phenyl-2-cyclohexylethanes, 1-cyclohexyl-2-(4-phenylcyclohexyl)-ethanes, trans-1-cyclohexyl-2-(4-phenylcyclohexyl)-ethenes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of novel media can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe. or Phe-Cyc. The novel media preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the subformulae 1a, 2a, 3a, 4a and 5 a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+l)}$F$_k$Cl$_1$, where i is 0 or 1, and k+l is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b, 5b and 6b in which R" is —F, —Cl, —NCS, —CF$_3$, —OCHF$_2$ or —OCF$_3$.

In the compounds of the sub-formulae 1b, 2b, 3b, 4b, and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides novel compounds of the formula I, the novel media preferably comprise one or more compounds selected from group A and/or group B and/or group C. The proportions by weight of the compounds from these groups in the novel media are preferably:

Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular novel media preferably being 5%–90% and in particular 10% to 90%.

The novel media preferably comprise 1 to 40%, particularly preferably 5 to 30%, of novel compounds. Further preferred media are those which comprise more than 40%, in particular 45 to 70%, of novel compounds. The media preferably comprise three, four or five novel compounds.

The novel media are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 196 47 991.6, filed Nov. 20, 1996, is hereby incorporated by reference.

EXAMPLES

The examples below are intended to illustrate the invention without representing a limitation. Above and below, percent data are percent by weight. All temperatures are given in degrees Celsius. mp.=melting point, cp.=clearing point. Furthermore, C=crystalline state, N=nematic phase, Sm=smectic phase and I=isotropic phase. The number between two symbols indicates the conversion temperature in degrees Celsius. Δn denotes optical anisotropy (589 nm, 20° C.), and the viscosity (mm$^2$/sec) was determined at 20° C.

"Conventional work-up" means that water is added if necessary, the mixture is extracted with dichloromethane, diethyl ether, or toluene, the organic phase is separated off, dried and evaporated, and the product is purified by distillation under reduced pressure or crystallization and/or chromatography.

The following abbreviations are used:

DCC dicyclohexylcarbodiimide
DMAP p-dimethylaminopyridine
KOtBu potassium tert-butoxide
Me$_3$SiOTf trimethylsilyl trifluoromethanesulfonate
THF tetrahydrofuran
TsOH p-toluenesulfonic acid

EXAMPLE 1 trans/trans-4'-(2,2-difluorovinyloxymethyl)-4-pentylbicyclohexyl a) trans/trans-4'-pentylbicyclohexyl-4-ylmethyl formate 26.6 g of trans/trans-(4'-(pentylbicyclohexyl-4-yl)-methanol are dissolved in 150 ml of dichloromethane, and 6.0 g of formic acid and 1.2 g of DMAP are added. A solution of 24.6 g of DCC in 100 ml of dichloromethane is added dropwise at 5–10° C., and the mixture is stirred overnight at room temperature. 1.8 g of oxalic acid are added, the mixture is filtered, and the filtrate is purified on silica gel. Evaporation gives 28.0 g of trans/trans-4'-pentylbicyclohexyl-4-ylmethyl formate.

b) trans/trans-4'-(2,2-difluorovinyloxymethyl)-4-pentylbicyclohexyl 3.8 ml of dibromodifluoromethane are added at 5° C. to a solution of 6.1 g of trans/trans-4'-pentylbicyclohexyl-4-ylmethyl formate in a mixture of 10 ml of THF and 100 ml of dioxane, and 15.2 ml of hexamethyltriamino-phosphine are subsequently added dropwise at 5–10° C. The mixture is stirred overnight at room temperature and subjected to conventional work-up, giving trans/trans-4'-(2,2-diflurovinyloxymethyl)-4-pentylbicyclohexyl. mp.: −8 SmB 72 I, Δn=0.051, viscosity: 11 mm$^2$/s.

The following compounds are obtained analogously from the corresponding precursors:

Unless otherwise stated, $Z^1$ and $Z^2$ in Examples 2–21 are a single bond, l=1, $X^1$ and $X^2$ are simultaneously F. n is 1 and $A^3$ is Cyc.

| Example | R | $A^1$ | $Z^1$ | m | $A^2$ | $Z^2$ |
|---|---|---|---|---|---|---|
| 2 | Ethyl | Cyc | | 0 | | |
| 3 | n-Propyl | Cyc | | 0 | | |
| 4 | n-Butyl | Cyc | | 0 | | |
| 5 | n-Hexyl | Cyc | | 0 | | |
| 6 | n-Heptyl | Cyc | | 0 | | |
| 7 | Ethyl | Cyc | C$_2$H$_4$ | 0 | | |
| 8 | n-Propyl | Cyc | C$_2$H$_4$ | 0 | | |
| 9 | n-Butyl | Cyc | C$_2$H$_4$ | 0 | | |
| 10 | Ethyl | Cyc | | 1 | Cyc | |
| 11 | n-Propyl | Cyc | | 1 | Cyc | |
| 12 | n-Butyl | Cyc | | 1 | Cyc | |
| 13 | Ethyl | Phe | | 1 | Phe | |
| 14 | n-Propyl | Phe | | 1 | Phe | |
| 15 | n-Butyl | Phe | | 1 | Phe | |
| 16 | Ethyl | Cyc | C$_2$H$_4$ | 1 | Cyc | |
| 17 | n-Propyl | Cyc | C$_2$H$_4$ | 1 | Cyc | |
| 18 | n-Butyl | Cyc | C$_2$H$_4$ | 1 | Cyc | |
| 19 | Ethyl | Cyc | | 1 | Cyc | C$_2$H$_4$ |
| 20 | n-Propyl | Cyc | | 1 | Cyc | C$_2$H$_4$ |
| 21 | n-Butyl | Cyc | | 1 | Cyc | C$_2$H$_4$ |

EXAMPLE 22 trans/trans-4'-(2-fluorovinyloxymethyl)-4-pentylbicyclohexyl

By hydrogenation in the presence of Pd/C followed by a reaction with KOtBu in THF and conventional work-up, trans/trans-4'-(2-E-fluorovinyloxymethyl)-4-pentylbicyclohexyl or trans/trans-4'-(2-Z-fluorovinyloxymethyl)-4-pentylbicyclohexyl is obtained from trans/trans-4'-(2,2-difluorovinyloxymethyl)-4-pentylbicyclohexyl.

The following compounds are obtained analogously from the corresponding precursors:

Unless otherwise stated, $Z^1$ and $Z^2$ in Examples 23–45 are a single bond, l=1, $X^1$ is F and $X^2$ is H. n is 1 and $A^3$ is Cyc.

| Example | R | $A^1$ | $Z^1$ | m | $A^2$ | $Z^2$ |
|---|---|---|---|---|---|---|
| 23 | Ethyl | Cyc | | 0 | | |
| 24 | n-Propyl | Cyc | | 0 | | |
| 25 | n-Butyl | Cyc | | 0 | | |
| 26 | n-Hexyl | Cyc | | 0 | | |
| 27 | n-Heptyl | Cyc | | 0 | | |
| 28 | Ethyl | Cyc | C$_2$H$_4$ | 0 | | |
| 29 | n-Propyl | Cyc | C$_2$H$_4$ | 0 | | |
| 30 | n-Butyl | Cyc | C$_2$H$_4$ | 0 | | |
| 31 | Ethyl | Cyc | | 1 | Cyc | |
| 32 | n-Propyl | Cyc | | 1 | Cyc | |
| 33 | n-Butyl | Cyc | | 1 | Cyc | |
| 34 | Ethyl | Phe | | 1 | Phe | |
| 35 | n-Propyl | Phe | | 1 | Phe | |
| 36 | n-Butyl | Phe | | 1 | Phe | |
| 37 | Ethyl | Cyc | C$_2$H$_4$ | 1 | Cyc | |
| 38 | n-Propyl | Cyc | C$_2$H$_4$ | 1 | Cyc | |

-continued

| Example | R | $A^1$ | $Z^1$ | m | $A^2$ | $Z^2$ |
|---|---|---|---|---|---|---|
| 39 | n-Butyl | Cyc | $C_2H_4$ | 1 | Cyc | |
| 40 | Ethyl | Cyc | | 1 | Cyc | $C_2H_4$ |
| 41 | n-Propyl | Cyc | | 1 | Cyc | $C_2H_4$ |
| 42 | n-Butyl | Cyc | | 1 | Cyc | $C_2H_4$ |
| 43 | Ethyl | Dio | | 0 | | |
| 44 | n-Propyl | Dio | | 0 | | |
| 45 | n-Butyl | Dio | | 0 | | |

EXAMPLE 46 trans/trans-2-(2,2-difluorovinyloxymethyl)-5-(4-pentylcyclohexyl)-1,3-dioxane a) trans/trans-2-benzyloxymethyl-5-(4-pentylcyclohexyl)-1,3-dioxane A solution of 100 mmol of trans-2-(4-pentylcyclohexyl) propane-1,3-diol, 100 mmol of benzyloxyacetaldehyde and 10 mmol of p-toluenesulfonic acid in 500 ml of toluene is heated at the boil on a water separator until the water separation is complete. Conventional work-up gives trans/trans-2-benzyloxymethyl-5- (4-pentylcyclohexyl)-1,3-dioxane.

b) trans/trans -[5-(4-pentylcyclohexyl)-1,3-dioxan-2-yl]methanol

A solution of 100 mmol of trans/trans-2-benzyloxymethyl-5-(4-pentylcyclohexyl)-1,3-dioxane is hydrogenated in 300 ml of THF with the addition of 2.0 g of 5% Pd/activated charcoal until the take-up of hydrogen is complete. trans/trans-[5-(4-pentylcyclohexyl)-1,3-dioxan-2-yl]methanol is obtained by conventional work-up.

c) trans/trans-2-(2,2-difluorovinyloxymethyl)-5-(4-pentylcyclohexyl)-1,3-dioxane 27.0 g of trans/trans-[5-(4-pentylcyclohexyl)-1,3-dioxan-2-yl]methanol are firstly esterified using formic acid as described in Example 1 and then treated with dibromodifluoromethane. Conventional work-up gives trans/trans-2-(2,2-difluorovinyloxymethyl)-5-(4-pentylcyclohexyl)-1,3-dioxane.

The following are prepared analogously:

Unless otherwise stated, $Z^1$ and $Z^2$ in Examples 47–57 are a single bond, l=1, $X^1$ and $X^2$ are simultaneously F. n is 1 and $A^3$ is Dio.

| Example | R | $A^1$ | $Z^1$ | m | $A^2$ | $Z^2$ |
|---|---|---|---|---|---|---|
| 47 | Ethyl | Cyc | | 0 | | |
| 48 | n-Propyl | Cyc | | 0 | | |
| 49 | n-Butyl | Cyc | | 0 | | |
| 50 | n-Hexyl | Cyc | | 0 | | |
| 51 | n-Heptyl | Cyc | | 0 | | |
| 52 | Ethyl | Cyc | | 1 | Cyc | |
| 53 | n-Propyl | Cyc | | 1 | Cyc | |
| 54 | n-Butyl | Cyc | | 1 | Cyc | |
| 55 | Ethyl | Phe | | 1 | Phe | |
| 56 | n-Propyl | Phe | | 1 | Phe | |
| 57 | n-Butyl | Phe | | 1 | Phe | |

EXAMPLE 58 trans/trans-2-[4-(2,2-difluorovinyloxymethyl) cyclohexyl]-5-pentyl-1,3-dioxane a) trans/trans-[4-(5-pentyl-1,3-dioxan-2-yl) cyclohexyl]methanol A solution of 100 mmol of 2-pentylpropane-1,3-diol, 100 mmol of trans-4-hydroxymethylcyclohexanecarbaldehyde and 10 mmol of p-toluenesulfonic acid in 500 ml of toluene is heated at the boil on a water separator until the water separation is complete. Conventional work-up gives trans/trans-[4-(5-pentyl-1,3-dioxan-2-yl)cyclohexyl]methanol.

b) trans/trans-2-[4-(2,2-difluorovinyloxymethyl) cyclohexyl]-5-pentyl-1,3-dioxane 27.0 g of trans/trans-[4-(5-pentyl-1,3-dioxan-2-yl)-cyclohexyl]methanol are firstly esterified using formic acid as described in Example 1 and then treated with dibromodifluoromethane. Conventional work-up gives trans/trans-2-[4-(2,2-difluorodivinyloxymethyl)cyclohexylI-5-pentyl-1,3-dioxane.

The following are prepared analogously:

Unless otherwise stated, $Z^1$ and $Z^2$ in Examples 59–66 are a single bond, l=1, $X^1$ and $X^2$ are simultaneously F. n is 1 and $A^3$ is Cyc.

| Example | R | $A^1$ | $Z^1$ | m | $A^2$ | $Z^2$ |
|---|---|---|---|---|---|---|
| 59 | Ethyl | Dio | | 0 | | |
| 60 | n-Propyl | Dio | | 0 | | |
| 61 | n-Butyl | Dio | | 0 | | |
| 62 | n-Hexyl | Dio | | 0 | | |
| 63 | n-Heptyl | Dio | | 0 | | |
| 64 | Ethyl | Dio | | 1 | Cyc | |
| 65 | n-Propyl | Dio | | 1 | Cyc | |
| 66 | n-Butyl | Dio | | 1 | Cyc | |

EXAMPLE 67 trans/trans-2'-(2,2-difluorovinyloxymethyl)-5-pentyl-2,5'-bi[1,3-dioxanyl]

a) trans/trans-2'-benzyloxymethyl-5-pentyl-2,5'-bi[1, 3-dioxanyl]

5 mmol of $Me_3SiOT_f$ are added at −78° C. to a solution of 120 mmol of trans-5-pentyl-2-(2-trimethylsilanyloxy-1-trimethylsilanyloxymethylethyl)-1,3-dioxane and 100 mmol of benzyloxyacetaldehyde in 300 ml of dichloromethane. The mixture is stirred at the same temperature for 3 hours, 300 mmol of pyridine are added, and the mixture is poured into a saturated $NaHCO_3$ solution. The mixture is subjected to conventional work-up. The trans-isomer of trans/trans-2'-benzyloxymethyl-5-pentyl-2,5'-bi[1,3-dioxanyl] is isolated by crystallization from ethanol.

b) trans/trans-(5-pentyl]2,5'-bi[1,3-dioxanyl]-2'-yl) methanol

A solution of 100 mmol of trans/trans-2'-benzyloxymethyl-5-pentyl-2,5'-bi[1;3-dioxanyl] is hydrogenated in 300 ml of THF with addition of 2.0 g of 5% Pd/activated charcoal until the take-up of hydrogen is complete. trans/trans-(5-pentyl-2,5'-bi[1,3-dioxanyl]-2'-yl) methanol is obtained by conventional work-up.

c) trans/trans-2'-(2,2-difluorovinyloxymethyl)-5-pentyl-2,5'-bi[1,3-dioxanyl]

28.0 g of trans/trans-(5-pentyl-2,5'-bi[1,3-dioxanyl]-2'-yl) methanol are firstly esterified using formic acid as described in Example 1 and then treated with dibromodifluoromethane. Conventional work-up gives trans/trans-2'-(2,2-difluorovinyloxymethyl)-5-pentyl-2,5'-bi[1,3-dioxanyl].

The following are prepared analogously:

Unless otherwise stated, $Z^1$ and $Z^2$ in Examples 68–78 are a single bond, l=1, $X^1$ and $X^2$ are simultaneously F. n is 1 'and $A^3$ is Dio.

| Example | R | $A^1$ | $Z^1$ | m | $A^2$ | $Z^2$ |
|---|---|---|---|---|---|---|
| 68 | Ethyl | Dio | | 0 | | |
| 69 | n-Propyl | Dio | | 0 | | |
| 70 | n-Butyl | Dio | | 0 | | |
| 71 | n-Hexyl | Dio | | 0 | | |
| 72 | n-Heptyl | Dio | | 0 | | |
| 73 | Ethyl | Phe | | 1 | Dio | |
| 74 | n-Propyl | Phe | | 1 | Dio | |
| 75 | n-Butyl | Phe | | 1 | Dio | |
| 76 | Ethyl | Cyc | | 1 | Dio | |
| 77 | n-Propyl | Cyc | | 1 | Dio | |
| 78 | n-Butyl | Cyc | | 1 | Dio | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A halovinyl ether compound of formula I

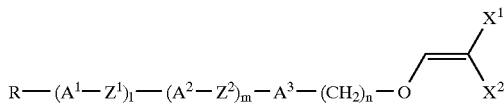

in which

R is alkyl or alkenyl having 1 to 12 carbon atoms, wherein one or more $CH_2$ groups are optionally replaced by —O—, —$CF_2$— or —CH=CH—, or one or two CH groups are optionally replaced by CF, in such a way that two oxygen atoms are not linked to one another, $A^1$, $A^2$ and $A^3$ are each, independently of one another,
  a) a trans-1,4-cyclohexylene radical, in which, one or more non-adjacent $CH_2$ groups are optionally replaced by —O— and/or —S—,
  b) a 1,4-phenylene radical, in which, one or two CH groups are optionally replaced by N,
  c) a radical selected from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, or
  d) 1,4-cyclohexenylene, where the radicals a), b) and d) are optionally substituted by one or two Cl or F atoms, $Z^1$ and $Z^2$ are each, independently of one another, —CO—O—, —O—CO—, —$CH_2$O—, —O—$CH_2$—, —$CH_2CH_2$—, —CH=CH—, —C≡C— or a single bond, $X^1$ and $X^2$ are each, independently of one another, H, Cl or F, provided that at least one of $X^1$ and $X^2$ is Cl or F, l and m are each independently of one another, 0, 1 or 2, where l+m is 24 1, and n is 1, 2 or 3.

2. A halovinyl ether compound of the formula I according to claim 1, wherein $X^1$ and $X^2$ are each fluorine.

3. A halovinyl ether compound according to claim 1, wherein n=1 and $A^3$ is:

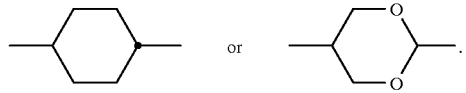

4. A halovinyl ether compound according to claim 2, wherein n=1 and $A^3$ is:

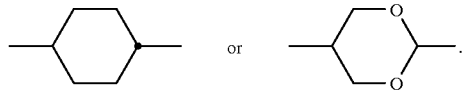

5. A halovinyl ether compound according to claim 1, wherein R is an alkyl radical in which one or more $CH_2$ groups are optionally replaced by —O— or $CF_2$.

6. A halovinyl ether compound of claim 1, which is a difluorovinyl ether of one of the formulae Ia to Id;

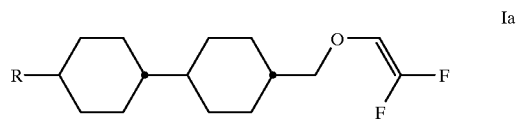

Ia

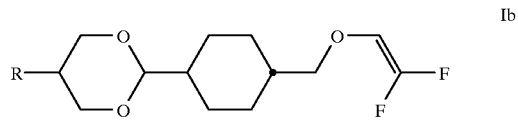

Ib

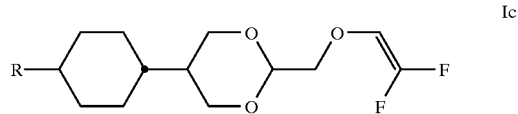

Ic

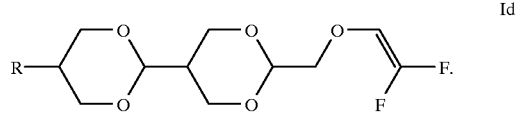

Id

7. A liquid-crystalline medium having at least two liquid-crystalline components, wherein at least one component is a compound of the formula I of claim 1.

8. A liquid-crystalline medium having at least two liquid-crystalline components, wherein at least one component is a compound of the formula Ia to Id of claim 6.

9. A liquid-crystal display element which contains a liquid-crystalline medium according to claim 7.

10. A liquid-crystalline display element which contains a liquid-crystalline medium according to claim 8.

11. An electro-optical display element, which contains, as dielectric, a liquid-crystalline medium according to claim 7.

12. An electro-optical display element, which contains, as dielectric, a liquid-crystalline medium according to claim 8.

13. A halovinyl ether compound of claim 1, wherein n=1.

* * * * *